(12) United States Patent
Day et al.

(10) Patent No.: US 9,778,195 B2
(45) Date of Patent: Oct. 3, 2017

(54) METHOD AND DETECTOR FOR DETECTING AN ANALYTE

(71) Applicant: Nederlandse Organisatie voor toegepast—natuurwetenschappelijk onderzoek TNO, 's-Gravenhage (NL)

(72) Inventors: James Peter Robert Day, 's-Gravenhage (NL); Marijn Sandtke, 's-Gravenhage (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 45 days.

(21) Appl. No.: 14/893,322

(22) PCT Filed: May 23, 2014

(86) PCT No.: PCT/NL2014/050329
§ 371 (c)(1),
(2) Date: Nov. 23, 2015

(87) PCT Pub. No.: WO2014/189379
PCT Pub. Date: Nov. 27, 2014

(65) Prior Publication Data
US 2016/0116414 A1    Apr. 28, 2016

(30) Foreign Application Priority Data

May 24, 2013   (EP) ..................................... 13169244

(51) Int. Cl.
*G01J 3/44* (2006.01)
*G01N 21/65* (2006.01)
(Continued)

(52) U.S. Cl.
CPC .......... *G01N 21/65* (2013.01); *B01D 53/1425* (2013.01); *B01D 53/1475* (2013.01);
(Continued)

(58) Field of Classification Search
CPC .......... G01N 21/65; G01N 21/49; G01N 1/44; G01D 53/18; G01D 53/14; G01J 3/44
See application file for complete search history.

(56) References Cited

U.S. PATENT DOCUMENTS 5,949,532 A  *  9/1999  Schrof ...................... G01J 3/44
                                                  250/458.1
2004/0127778 A1    7/2004  Lambert et al.
(Continued)

FOREIGN PATENT DOCUMENTS

WO    2013/023919 A1    2/2013

OTHER PUBLICATIONS

Martins et al., "Shifted-excitation Raman difference spectroscopy for in vitro and in vivo biological samples analysis" Biomedical Optics Express 617, vol. 1, No. 2, Sep. 1, 2010 , 10 pages.
(Continued)

*Primary Examiner* — Abdullahi Nur
(74) *Attorney, Agent, or Firm* — Renner, Otto, Boisselle & Sklar, LLP

(57) ABSTRACT

The present disclosure concerns a method and detector (10) for detecting an analyte (1) in a sample volume (2), such as nitrosamine in an amine solvent. The method comprises measuring a resonance Raman spectrum (I1) with a first light beam (PI) matching an electronic transition of the analyte (1). The detection of the analyte is enhanced by measuring an off-resonance Raman spectrum (12) using a second light beam (P2) that is shifted in wavelength at least 10 nm away from the electronic resonance. The resonance Raman signal (S1) of the analyte (1) is isolated from the background (Q1, Q2) by a difference analysis between the resonance and off-resonance Raman spectra (I1, I2). The
(Continued)

method and detector (10) can be employed for detecting nitrosamine in a carbon capture process or plant (20) that employs an amine solvent.

14 Claims, 11 Drawing Sheets

(51) Int. Cl.
| | |
|---|---|
| *B01D 53/14* | (2006.01) |
| *B01D 53/62* | (2006.01) |
| *B01D 53/18* | (2006.01) |
| *G01N 1/44* | (2006.01) |
| *G01N 21/49* | (2006.01) |
| *G01N 21/84* | (2006.01) |

(52) U.S. Cl.
CPC ......... *B01D 53/1493* (2013.01); *B01D 53/18* (2013.01); *B01D 53/62* (2013.01); *G01J 3/44* (2013.01); *G01N 1/44* (2013.01); *G01N 21/49* (2013.01); *G01N 21/658* (2013.01); *B01D 2252/204* (2013.01); *B01D 2258/0283* (2013.01); *G01J 2003/4424* (2013.01); *G01N 2021/8416* (2013.01); *G01N 2201/0697* (2013.01); *G01N 2201/06113* (2013.01); *Y02C 10/06* (2013.01)

(56) References Cited

U.S. PATENT DOCUMENTS

| | | | |
|---|---|---|---|
| 2004/0234958 A1* | 11/2004 | Smith | C07D 213/53 435/6.12 |
| 2012/0162641 A1 | 6/2012 | Schmidt et al. | |

OTHER PUBLICATIONS

Grun et al., "Tunable-multi-wavelength resonance-Raman detection of bacteria and chemicals in complex environments", Proc. of SPIE, vol. 7687, 2010, pp. 768701-1-768706-12.

International Search Report and the Written Opinion for corresponding International Application No. PCT/NL2014/050329 dated Jul. 10, 2014.

* cited by examiner

METHOD AND DETECTOR FOR DETECTING AN ANALYTE

This application is a national phase of International Application No. PCT/NL2014/050329 filed May 23, 2014 and published in the English language, and claims priority to Application No. EP 13169244.4 filed May 24, 2013.

FIELD AND BACKGROUND

The present disclosure concerns a method for detecting an analyte, a carbon capture process comprising the method, a nitrosamine detector for detecting presence of a nitrosamine analyte in an amine solvent, and a carbon capture plant comprising the detector.

Contribution of the greenhouse gas carbon dioxide ($CO_2$) to global warming is well-documented. One promising step to limit the release of $CO_2$ to the environment e.g. from power plants, is through post-combustion carbon capture. In one example, $CO_2$ from flue gases is dissolved by an amine solvent in a carbon capture process or plant. The amine solvent comprises an aqueous solution of an amine such as monoethanolamine ("MEA"), to form carbonate and carbamate ions. Unfortunately, a by-product of this approach can be the formation in the amine solvent of nitrosamines such as N-nitrosodiethanolamine ("NDELA"), e.g. from a reaction of amines with nitrogen oxide compounds (NOx) that may be present in the flue gas. Such nitrosamines are considered to be carcinogenic even at very low concentrations, e.g. a few parts per million (ppm). Therefore, for carbon capture processes using amine solvents to become more acceptable, there is a need to deal with the possible nitrosamine contamination.

For example, WO2013/023919 describes a method and device for purification of a nitrosamine-contaminated product from a process plant wherein the contaminated product is treated with UV radiation from a UV light source such that nitrosamines are destroyed. There remains a desire for an improved method and/or detector for detecting the presence and/or concentration of nitrosamines in the amine solvent, e.g. to determine whether a treatment is efficient or even necessary at all. More in general there is a need for a detection method having improved specificity and sensitivity to a selected analyte which method can be implemented inline for continuous monitoring of a process flow such as carbon capture.

SUMMARY

A first aspect of the present disclosure provides a method for detecting an analyte in a sample volume, the analyte having an electronic transition, the method comprising directing a first light beam having a first wavelength into the sample volume, wherein the first wavelength matches the electronic transition of the analyte for generating a resonance Raman signal of the analyte; measuring a first Raman spectrum from the sample volume, the first Raman spectrum comprising the resonance Raman signal of the analyte and a first Raman background generated by the first light beam interacting in the sample volume; directing a second light beam having a second wavelength into the sample volume, wherein the second wavelength is shifted with respect to the first wavelength away from the electronic transition for generating an off-resonance Raman signal of the analyte, wherein the off-resonance Raman signal is lower than the resonance Raman signal; measuring a second Raman spectrum from the sample volume, the second Raman spectrum comprising the off-resonance Raman signal and a second Raman background generated by the second light beam interacting in the sample volume; and calculating the resonance Raman signal of the analyte from a difference analysis between the first and second Raman spectra.

By measuring a resonant Raman spectrum using a first pump wavelength that is specifically tuned to an electronic transition or resonance of the analyte to be detected, the Raman signal of the analyte is enhanced compared to any off-resonance background Raman signals. This can provide a detection method having improved specificity for the selected analyte. Furthermore, by using a second pump wavelength that is tuned away from the electronic resonance of the analyte, a reference or off-resonance Raman spectrum is obtained wherein the Raman signal of the analyte is not enhanced or less enhanced, while the non-resonant background Raman spectrum is affected less or not at all by the change in pump wavelength. By a difference analysis between the resonant and reference Raman spectra, the resonant Raman signal of the analyte, measured predominantly in the resonant Raman spectrum, can be enhanced or isolated while a contribution of the non-resonant background of the solvent and other solutes in the Raman spectrum can be removed or compensated. By removing or compensating the non-resonant background, a higher signal over background ratio is obtained providing an improved detection sensitivity of the resonant signal, i.e. the selected analyte. Thus, by using multiple light beams having different wavelengths for pumping resonant and non-resonant transitions of the analyte, and comparing the resulting different Raman spectra, a detection method having improved specificity and sensitivity is provided.

Furthermore, because the method measures a reference spectrum of the sample volume to subtract the background, a changing condition of the solvent can be compensated automatically. This makes the method suitable to be implemented inline for continuous monitoring of a process flow, in particular a process flow experiencing rapidly changing conditions, e.g. differing concentrations of solutes. By the dynamic subtraction of background signals, the method can be more robust in handling unexpected or unknown variations of the process flow. Furthermore, the method does not require any scanning or moving parts and can thus rapidly perform a detection of multiple spectra before changes in the process flow occur which changes may skew the reference spectra. By directing the first and second light beams to generate the resonance Raman signal and the off-resonance Raman signal at different locations in the sample volume, the said different locations can be imaged separately on the detector, e.g. by suitable projection optics. In this way interference between the signals can be minimized and the signals can be measured in parallel. By directing the light beams with distinct wavelengths simultaneously into the sample volume, the resonance and off-resonance Raman spectra can be recorded simultaneously and a relatively fast detection is provided. By passing a sample flow through the sample volume while repeatedly calculating the resonance Raman signal of the analyte, a process flow can be monitored continuously e.g. for changes in concentrations.

It is noted that US 2012/0162641 describes shifted-excitation Raman difference spectroscopy (SERDS) to eliminate a fluorescence background. While it is stated in this prior art that SERDS may be used in combination with other Raman techniques (e.g., SERS and resonance Raman spectroscopy), the specific combination of resonance and off-resonance spectra is not disclosed. Moreover, it is not disclosed how the prior art algorithm which relies on differences between off-resonance Raman signals, can be adapted to handle a combination of resonance and off-resonance spectra. Furthermore, according to the prior art method, the medium to be analysed is exposed in a time-shifted manner to first and second excitation radiation. Accordingly, the simultaneous excitation using two beams is not suggested. Also excitation at different locations in the sample is not suggested.

It is noted that US 2004/0127778 describes non-invasive spectrographic analysis of certain regions of the eye, such as the aqueous humor in the anterior chamber of the eye. In certain embodiments, for certain substances having molecules that generate resonant Raman spectra, the signal strength can be greatly enhanced for certain excitation wavelengths that, in turn, may reduce the amount of the analyte that is detectable over non-resonant Raman spectra at that wavelength. In certain other embodiments, the fluorescence spectrum for the aqueous humor can be subtracted from the Raman spectrum by stimulating the aqueous humor with a second excitation laser light pulse at a wavelength slightly different from that of the first pulse (e.g., up to two nanometers from the first pulse). However a difference analysis between on-resonance and off-resonance spectra is not disclosed. It is noted that a wavelength shift up to two nanometers is typically insufficient to move off-resonance. Furthermore, excitation at different locations in the anterior chamber of the eye is not suggested.

A second aspect of the present disclosure provides a carbon capture process comprising providing a flue gas comprising carbon dioxide; providing an amine solvent; passing the flue gas via the amine solvent for dissolving carbon dioxide from the flue gas into the amine solvent; providing the amine solvent in a sample volume; and using a Raman spectroscopy method, e.g. according to the first aspect, for detecting presence of nitrosamine as analyte in the sample volume. It is presently recognized by the inventors that a method according to the first aspect is especially suitable for detecting minute concentrations of nitrosamines that typically occur in the amine solvent of the carbon capture process, in particular due to the aforementioned tuneable specificity, high sensitivity, and inline applicability of the method as well as the specific Raman spectra of the amine solvent, dissolved carbon dioxide, and nitrosamine analyte.

A third aspect of the present disclosure provides a nitrosamine detector for detecting presence of a nitrosamine analyte in an amine solvent, the detector comprising a sample chamber, arranged for providing the amine solvent in a sample volume; a first light source, arranged for directing a first light beam having a first wavelength into the sample volume, wherein the first wavelength matches an electronic transition of the analyte for generating a resonance Raman signal of the analyte; a first photo detector, arranged for measuring a first Raman spectrum from the sample volume, the first Raman spectrum comprising the resonance Raman signal of the analyte and a first background generated by the first light beam interacting in the sample volume; a processor, arranged for receiving the first Raman spectrum from the first photo detector, calculating the resonance Raman signal in the first Raman spectrum, and determining a presence and/or concentration of the analyte from the calculated Raman signal.

The detector according to the third aspect provides an advantageous implementation of a resonance Raman process that make it particularly suitable for the said specific implementation. The inventors found that the specific band structures of the nitrosamine analyte and the amine solvent (including dissolved flue gases) allow a resonant electronic transition of nitrosamine to be specifically targeted by a first wavelength of the sensor and the resulting resonant Raman signal isolated from the amine solvent background. Furthermore by using a second pump beam at a non-resonant wavelength, e.g. according to the method of the first aspect, the resonant Raman signal can be further enhanced from a difference analysis, thus allowing lower concentrations to be measured. This makes the sensor especially suitable for detecting minute (ppm) concentrations of nitrosamines in an amine solvent.

A fourth aspect of the present disclosure provides a carbon capture plant for the capture of carbon dioxide from a flue gas by means of an amine solvent, the plant comprising a detector according to the third aspect, arranged for detecting presence of nitrosamine in the amine solvent.

By providing a sensor that is sensitive to minute traces of nitrosamine in the amine solvent of a carbon capture plant, the formation of nitrosamine can be monitored. By said monitoring, it can be ensured that the nitrosamine concentration stays below limits for preventing the carcinogenic substance from causing harm. By providing continuous and inline monitoring of the nitrosamine concentration, the process flow of the carbon capture plant does not have to be interrupted. Upon detection of nitrosamine concentration above a pre-set limit, appropriate measures can be taken for preventing contact with the nitrosamine, preventing escape of the nitrosamine, preventing the further creation of nitrosamine, and/or lowering the nitrosamine concentration. In one example, process conditions such as the acidity of the amine solvent is adjusted for lowering a reaction rate leading to the creation of nitrosamine. In another or further example, UV light is used for breaking down nitrosamine, e.g. as described in WO2013/023919.

It is noted that US 2004/0234958 describes methods for detecting analytes such as explosives and drugs. It is described that sensitivity of Raman scattering may be improved by surface enhanced Raman scattering (SERS). Combining SERS and resonance Raman scattering to give surface enhanced resonance Raman scattering (SERRS), provides more sensitivity. SERRS detection may be conducted between about 300 nm-1100 nm. While the selection and tuning of an appropriate light source, is within the capabilities of one of ordinary skill in the art, the prior art does not disclose or suggest to provide a light source with a resonance wavelength that matches the electronic transition of a nitrosamine analyte in an amine solvent. Instead the prior art teaches to adapt the analyte by derivatisation with a chromophore having a resonance matching the laser chosen for the SERRS analysis. However, introducing pollutants by mixing the sample with a reagent is not desirable in a carbon capture plant.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1A:
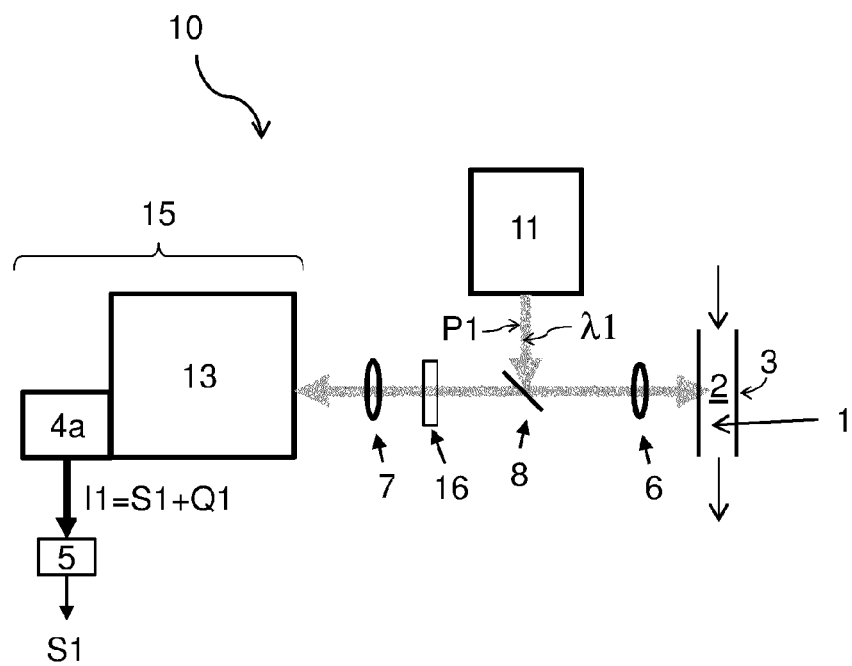
FIG. 1A shows an embodiment of a nitrosamine detector.

Unless otherwise defined, all terms (including technical and scientific terms) used herein have the same meaning as commonly understood by one of ordinary skill in the art to which this invention belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise. All publications, patent applications, patents, and other references mentioned herein are incorporated by reference in their entirety. In case of conflict, the present specification, including definitions, will control.

Raman spectroscopy is a spectroscopic technique that can be used to observe vibrational, rotational, and/or other low-frequency modes in a sample, e.g. molecules of interest. It is said to rely on inelastic scattering, or Raman scattering, of an incoming light beam, usually a monochromatic light beam, usually from a laser in the visible, near infrared, or near ultraviolet range. Preferably, for the present applications, the light source comprises a continuous (CW) laser for efficient generation of the Raman signals and suppression of photochemical degradation effects. Furthermore, the typically high peak powers in a pulsed UV beam may lead to undesired break down of the sample. The light beam interacts with molecular vibrations, phonons or other excitations in the sample, resulting in the energy of the photons in the scattered light being shifted up or down. The shift in energy of the scattered light with respect to that of the incoming beam can give information about the vibrational modes in the system and/or be used to analyze the system, e.g. determine the presence and/or concentration of an analyte.

Raman spectroscopy can be used to analyze e.g. gaseous, liquid, and solid samples. Samples can be put in a sample chamber and/or flowed via the sample chamber. To further enhance a Raman scattering signal, the sample chamber can be placed between two mirrors that reflect the light beam multiple times through the sample. Since the scattered light, carrying the Raman signal, can in principle leave the sample in all directions, a detector and/or light guides (e.g. lenses, mirrors, fibres) that collect and/or carry the scattered light back to the detector, may be placed at any accessible angle. In one common arrangement, the light guide is positioned in a backscattering configuration, e.g. at 180° with respect to the incident light. The scattered radiation that is captured from the sample, is usually sent through a dispersing and/or diffracting element such as a monochromator or spectrometer to select a specific wavelength or range of wavelengths. Typical monochromators or spectrometers may comprise a wavelength resolving element such as a prism and/or diffraction grating. E.g. by adjusting an angle of the grating, it can be controlled which wavelengths of scattered radiation reach a detecting element, e.g. a photo detector arranged for measuring an intensity of light falling on the detecting element. The detecting element itself can e.g. be a single pixel detector or a multi-pixel array detector such as a charge-coupled device (CCD), which allows simultaneous measuring of the spectrum at multiple wavelengths.

In resonance Raman spectroscopy, an energy of an incoming light beam is adjusted such that the energy of the incoming beam and/or of the scattered light matches an electronic transition of a molecule of interest, i.e. the analyte. In other words a photon energy of the incoming light beam matches an energy difference between an initial electronic state and an electronically excited state of the analyte, i.e. the photon has the same energy or is at least close in energy as the said energy difference. An electronically excited state may be thought of as arising from the promotion of one of the electrons from the occupied orbital e.g. in the ground state to a vacant higher energy orbital. Resonance Raman spectroscopy may be contrasted with regular (off-resonance) Raman spectroscopy wherein the energy of the incoming light pumps the system to a virtual intermediate state which is not an electronically excited state.

Of course it will be understood that in a real physical system, there can be a spread in the energies that more or less match a resonant electronic transition of an analyte. For example, an absorption line width of the analyte indicating the electronic resonance can be spread over a certain wavelength range. The terms resonant and off-resonant may thus be considered relative terms indicating a better or worse matching between the energy of the incoming light beam and the energy difference of the electronic transition. When the energy of the incoming light beam comes closer to that of the electronic transition, it can be observed that the Raman scattering is resonantly enhanced, i.e. a resonance Raman signal is expected to be higher than an off-resonance Raman signal. An advantage of resonance Raman spectroscopy over traditional (off-resonance) Raman spectroscopy is thus an increase in intensity of the desired signal, e.g. that of the analyte. This allows lower concentrations of an analyte to be detected.

Very often, the limiting factor in Raman-based spectroscopies (spontaneous Raman, resonance Raman, coherent anti-Stokes Raman scattering (CARS), stimulated Raman scattering (SRS) etc.) is not the strength of the Raman signal itself. Rather, the difficulty is discriminating this signal against a background signal arising e.g. from fluorescence or the large Raman signal from the solvent or matrix. Although increasing the number of photons collected by better optical design may increase the signal-to-noise ratio (SNR), this improvement alone does not always lead to superior sensing. In one aspect, the present disclosure provides a new technique for discrimination in resonance Raman spectroscopy: dual-pump resonance Raman spectroscopy (DP-RR).

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

FIG. 1A shows an embodiment of a method and nitrosamine detector 10 for detecting presence of a nitrosamine analyte 1 in an amine solvent. The detector 10 comprises a sample chamber 3, a first light source 11, a first photo detector 4a, and a processor 5. The sample chamber 3 is arranged for providing the amine solvent in a sample volume 2. The first light source 11 is arranged for directing a first light beam P1 having a first wavelength λ1 into the sample volume 2. The first wavelength λ1 matches an electronic transition of the nitrosamine analyte 1 for generating a resonance Raman signal S1 of the nitrosamine analyte 1. As described in the table below, preferably the first wavelength λ1 is between 240-250 nm to match an electronic transition of the nitrosamine analyte. The first photo detector 4a is arranged for measuring a first Raman spectrum I1 from the sample volume 2. The first Raman spectrum I1 comprises the resonance Raman signal S1 of the analyte 1 and a first non-resonant (Raman) background Q1 generated by the first light beam P1 interacting in the sample volume 2. As described below, preferably a resonance Raman signal at 1410 cm$^{-1}$ is detected. The processor 5 is arranged for receiving the first Raman spectrum I1 from the first photo detector 4a. The processor is further arranged for calculating the resonance Raman signal S1 in the first Raman spectrum I1. The processor is further arranged for determining a presence and/or concentration of the analyte 1 from the calculated Raman signal S1.

Correspondingly, a method for detecting presence of a nitrosamine analyte 1 in an amine solvent is disclosed. The method comprises providing the amine solvent in a sample volume 2. The method further comprises directing a first light beam P1 having a first wavelength λ1 into the sample volume 2, wherein the first wavelength λ1 matches an electronic transition ET of the analyte 1 for generating a resonance Raman signal S1 of the analyte 1. The method further comprises measuring a first Raman spectrum I1 from the sample volume 2, the first Raman spectrum I1 comprising the resonance Raman signal S1 of the analyte 1 and a first background Q1 generated by the first light beam P1 interacting in the sample volume 2 The method further comprises calculating the resonance Raman signal S1 in the first Raman spectrum I1, and determining a presence and/or concentration of the analyte 1 from the calculated Raman signal S1. Preferably, the first wavelength λ1 is between 240-250 nm. Preferably a resonance Raman signal at 1410 cm$^{-1}$ is detected.

In one embodiment, the first wavelength λ1 is 244 nm, and the calculating the resonance Raman signal S1 comprises calculating a spectral intensity at a Raman shift of 1410 cm$^{-1}$ as illustrated with reference to FIG. 1B by the dash dotted line. For example, in one embodiment, the output from a 244-nm UV laser 11 is directed by a dichroic mirror 8 and focused with a lens 6 onto a flowing sample 2 contained within a glass tube 3. The Raman scattered light is collected with the same lens 6 and passes through the dichroic mirror 8 and a 244 nm notch filter 16. An optical notch filter may e.g. rely on destructive interference of wavelengths not matching a desired pass band. Rayleigh-scattered light is e.g. rejected by the notch filter 16. The filtered Raman light is focused onto the entrance slit of a spectrograph 13. The light is dispersed within the spectrograph 13 and detected on a CCD array 4a. The detected signal I1 of the Raman spectrum is received from the photo detector 4a by a processor 5 which calculates the resonance Raman signal S1.

Figure 1B:
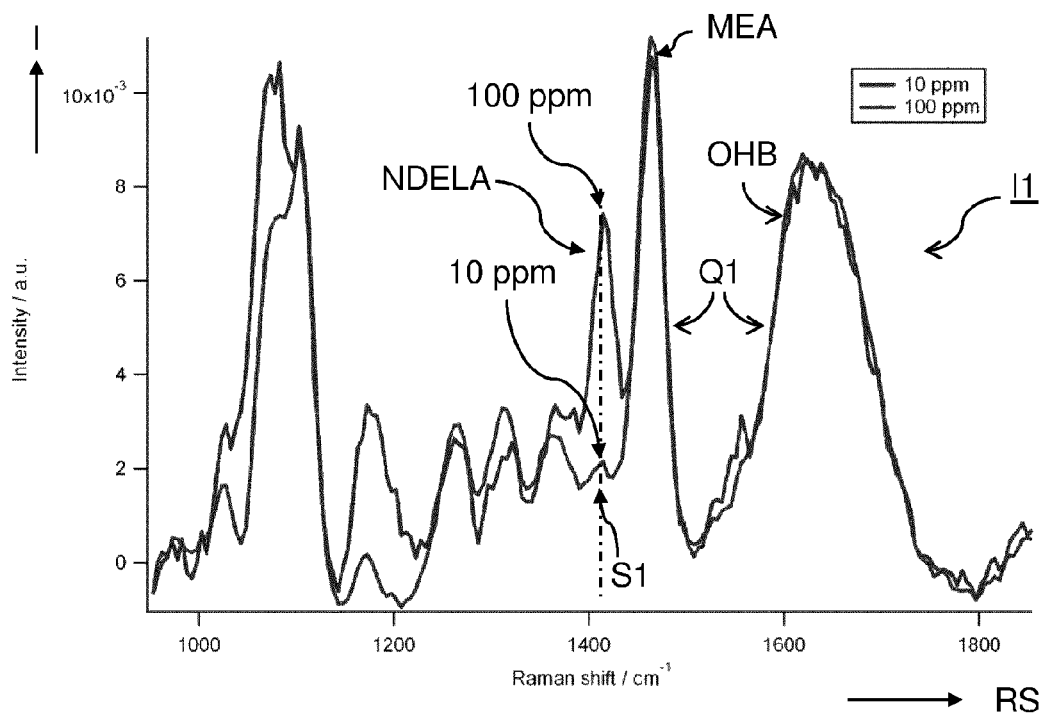
FIG. 1B shows resonance Raman spectra of nitrosamines in amine solutions.

FIG. 1B shows resonance Raman spectra of 10 ppm and 100 ppm NDELA in 1M (Molar) MEA solutions obtained with a detector as described in FIG. 1A having a pump wavelength λ1 at 244 nm. A peak in the NDELA spectrum is found at 1410 cm$^{-1}$. This peak is associated with the nitroso N=O vibration which can be resonantly enhanced in the deep UV region. For reference, with non-resonant Raman spectroscopy e.g. at 785 nm, the lowest concentration at which NDELA can typically be detected is around ~10,000 ppm. The nitroso peak at 1410 cm$^{-1}$ from NDELA is clearly visible even at 10 ppm in 1M MEA. In addition, the strong intensity (I) peak at a Raman shift (RS) of 1460 cm$^{-1}$ can be assigned to MEA. The Raman signal from MEA is not resonantly enhanced at 244 nm, but is detectable nonetheless through a non-resonant Raman process owing to its high concentration in the solution. The intensity (I) of the peak at 1460 cm$^{-1}$ considered to be linearly proportional to the concentration of MEA in solution. This experiment demonstrates that it is possible to detect NDELA with Resonant Raman spectroscopy at concentrations down to at least 10 ppm, both in water and in MEA solutions. This limit may be extended to lower concentrations e.g. by using the dual pump resonance Raman techniques as discussed herein. Simultaneously, it is possible to detect the concentration of MEA in solution. Although not shown here, it is also possible to quantify the concentration of dissolved $CO_2$ in amine solution by non-resonant Raman spectroscopy, e.g. as shown in the article by V. Souchon et al., Energy Procedia 4 (2011) 554-561. For example, a strong peak at 1015 cm$^{-1}$ can be indicative of the presence of carbonate in solution.

Accordingly, one embodiment of the resonance Raman method for detecting nitrosamine further comprises using off-resonant Raman signals in a Raman spectrum I1 for calculating a concentration of amines and/or dissolved carbon dioxide in the sample volume.

The concentrations of nitrosamines, amines and dissolved $CO_2$ can thus be determined from the Raman peaks at 1410 cm$^{-1}$, 1460 cm$^{-1}$ and 1015 cm$^{-1}$, respectively. Accordingly an integrated nitrosamine, amine and dissolved CO$_2$ sensor based on resonance and non-resonance Raman spectroscopy is provided.

Figure 2A:
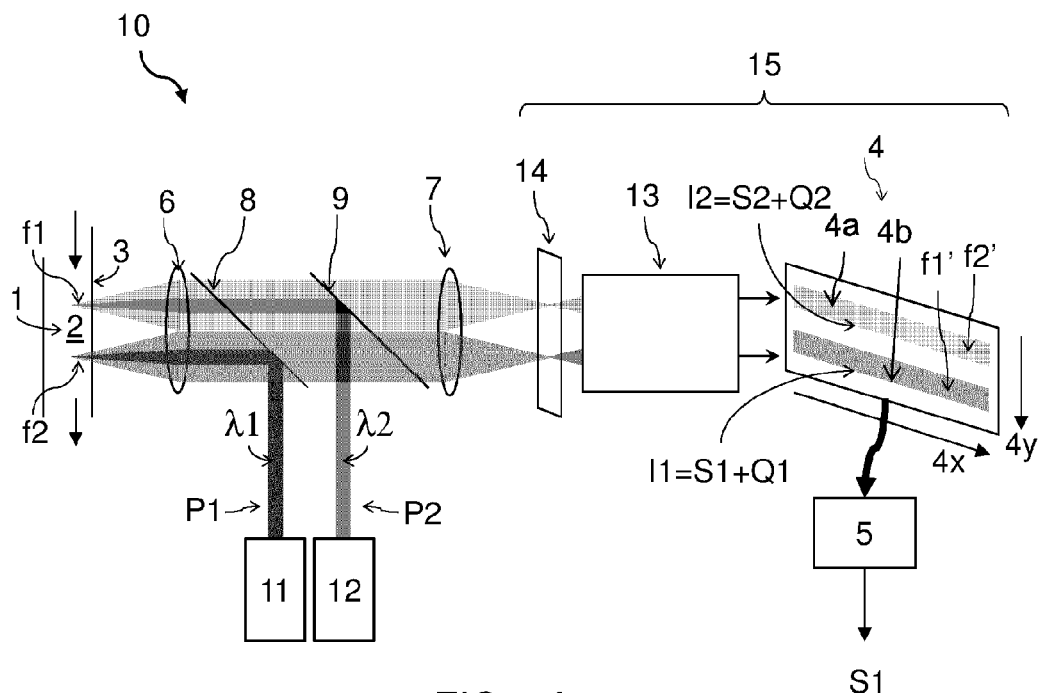
FIG. 2A shows a schematic embodiment of a method and detector for detecting an analyte.

FIG. 2A shows a schematic embodiment of method for detecting an analyte 1 in a sample volume 2. The method comprises directing a first light beam P1 having a first wavelength λ1 into the sample volume 2. The first wavelength λ1 matches an electronic transition of the analyte 1 for generating a resonance Raman signal S1 of the analyte 1. The method further comprises measuring a first Raman spectrum I1 from the sample volume 2. The first Raman spectrum I1 comprises the resonance Raman signal S1 of the analyte 1 and a first background Q1 generated by the first light beam P1 interacting in the sample volume 2. The method further comprises directing a second light beam P2 having a second wavelength λ2 into the sample volume 2. The second wavelength λ2 is shifted with respect to the first wavelength λ1 away from the electronic transition for generating an off-resonance Raman signal S2 of the analyte 1. The off-resonance Raman signal S2 is lower than the resonance Raman signal S1. The method further comprises measuring a second Raman spectrum I2 from the sample volume 2. The second Raman spectrum comprises the off-resonance Raman signal S2 and a second background Q2 generated by the second light beam P2 interacting in the sample volume 2. These may both be considered as off-resonant Raman signals. The method further comprises calculating the resonance Raman signal S1 of the analyte 1 from a difference analysis between the first and second Raman spectra I1,I2.

In one embodiment, the first and second light beams P1,P2 generate the resonance Raman signal S1 and the off-resonance Raman signal S2 at different locations f1,f2 in the sample volume 2. The said different locations f1,f2 can be imaged separately on the photo detectors 4a and 4b, e.g. using projection optics that image the locations onto the photo detectors. For example, the different locations may be defined by focal points of the beams P1 and P2 in the sample volume 2. Preferably, the different locations f1,f2 are in proximity to each other to sample a similar sample volume 2. Preferably, the different locations f1,f2 are separated to be within the field of view of the focussing lens 6, but far enough apart to be separately registered by the photo detectors 4a, 4b, e.g. wherein the images f1',f2' are separated more than a resolution of the photo detector 4.

In one embodiment, the light beams P1 and/or P2 are focussed in the sample volume 2 close to an edge of the sample chamber 3, e.g. within 5 mm of the edge, preferably within 1 mm of the edge. By focussing the light beams close to the edge, reabsorption of Raman scattered light by the sample can be limited before reaching a detector outside the sample volume.

In one embodiment, the first and second light beams P1,P2 are directed simultaneously into the sample volume 2 and the first and second Raman spectra I1,I2 are measured simultaneously. For example, the light sources 11 and 12 can be active simultaneously.

In one embodiment, a sample flow is passed through the sample volume 2 while the resonance Raman signal S1 of the analyte 1 is repeatedly calculated.

In the embodiment, the method is performed by a detector 10 for detecting presence of an analyte 1 in a solvent. The detector 10 comprises a sample chamber 3, arranged for providing the solvent in a sample volume 2 of the chamber. The detector 10 comprises a first light source 11 and a second light source 12. The first light source 11 is arranged for directing the first light beam P1 into the sample volume 2. The second light source 12 is arranged for directing the second light beam P2 into the sample volume 2. The detector 10 comprises a first photo detector 4a and a second photo detector 4b. The first photo detector 4a is arranged for measuring the first Raman spectrum I1 from the sample volume 2 and the second photo detector 4b is arranged for measuring the second Raman spectrum I2 from the sample volume 2. The detectors 4a and 4b can separate or integrated, e.g. part of the same CCD chip, e.g. using different rows of a 2D array to record the two spectra. The detector 10 comprises a processor 5, arranged for receiving the first and second Raman spectra I1,I2 from the first and second photo detectors 4a, 4b and calculating the resonance Raman signal S1 of the analyte 1 from a difference analysis between the first and second Raman spectra I1,I2.

One specific implementation of the dual-pump resonance Raman concept can be as follows. Two laser sources 11 and 12, e.g. at λ1=244 nm and λ2=266 nm respectively, are focused onto a flowing solution in a sample volume 2 such that the foci f1,f2 are offset (the offset is exaggerated in this figure for illustration purposes). The Raman scattered light originating from each focus, is imaged onto the spectrograph slit 14, dispersed by the spectrograph optics 14 and imaged onto the CCD array 4 with the spectra offset along the spatial axis 4y and dispersed along the dispersion axis 4x.

In the shown embodiment, a first dichroic mirror 8 is arranged for reflecting the first light beam P1 while transmitting the second light beam P2 as well as the scattered light from the sample volume 2. Furthermore a second dichroic mirror 9 is arranged for reflecting the second light beam P2 while transmitting the first light beam P1 as well as the scattered light from the sample volume 2. A lens 6 is arranged to focus the first light beam P1 and second light beam P2 in different locations f1 and f2 in the sample volume 2. In the embodiment, the same lens 6 is used to collect the (back)scattered light from the foci f1 and f2. Collected light is passed to a second lens 7 that images the foci f1 and f2 onto a slit 14 of a spectrometer 15. The spectrometer 15 comprises a spectrally resolving device such as a monochromator 13 arranged to provide spectrally resolved images f1' and f2' of the said different locations f1 and f2 onto a first photo detector 4a and second photo detector 4b. The photo detectors are read out by a processor 5 which calculates the resonance Raman signal S1 from a difference analysis of the first Raman spectrum I1 and the second Raman spectrum I2.

It will be appreciated that many variations can be envisaged of the shown example embodiment while maintaining similar functionality for the systems and methods. For example, alternative or in addition to using lenses, also curved, e.g. parabolic mirrors can be used. Instead of using the same lens 6 for focussing the pump beams and collecting the scattered light, a separate collection lens can be used, e.g. to collect scattered light transmitted through to the other side of the sample chamber 3. Alternative to using a second lens 7 for focussing the light onto a slit, the collection lens 6 could also act as a focussing lens to focus light onto the slit. Instead of focussing the light beams P1,P2 using a single lens 6, separate lenses or other focussing optics can be used. Instead of dichroic mirrors 8,9, other means for directing the beams P1,P2 to the sample can be used. Instead of using separate light sources 11,12, a single light source can be used, e.g. wherein light of different wavelengths for the first and second light beams P1,P2 is selected from a broader bandwidth of the light source and/or wherein light of different wavelengths is created by non-linear processes from a single light source. The photo detectors 4a and 4b may be comprised in separate detectors or comprised in a single detector, e.g. a pixel array such as a CCD.

Figure 2B:
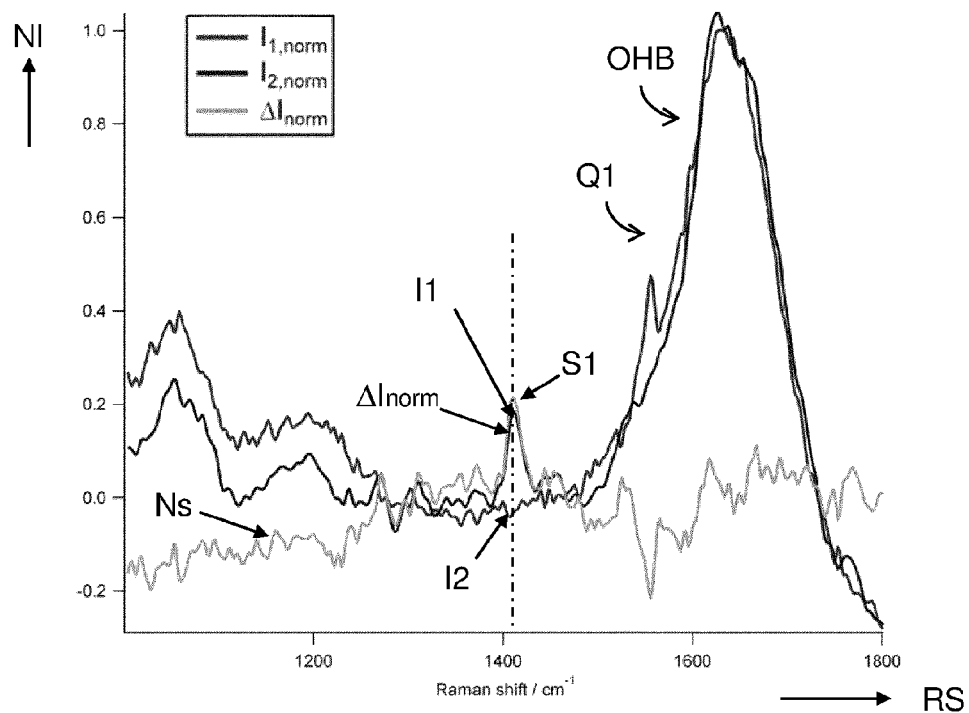
FIG. 2B shows an example difference analysis between first and second Raman spectra.

FIG. 2B shows an example difference analysis between first and second Raman spectra I1,I2 resulting in an enhanced resonance Raman signal S1. The figure shows normalized Raman spectra I1,I2 of 10-ppm NDELA in water taken at resonant and off-resonant pump wavelengths of $\lambda1=244$ and $\lambda2=266$ nm, respectively, as well as a difference spectrum $\Delta I_{norm}=I1-I2$. Although the noise level Ns is quite high, the difference spectrum $\Delta I_{norm}$ clearly shows the nitroso signal peak S1 at ~1410 cm$^{-1}$ that can be used to identify and/or measure the nitrosamine concentration, even if the signal and solvent peaks have more overlap than the current example.

In one embodiment, e.g. according to the example shown, the Raman spectra I1, I2 are normalized to an off-resonance signal present in the Raman spectra prior to the difference analysis. In the present example, the Raman spectra I1, I2 are normalized to a non-resonant peak of the HOH bending mode of water ("OHB") around a Raman shift of 1630 cm$^{-1}$. In general any non-resonant peak in the sample can be used to advantageously normalize the Raman spectra. By normalizing the Raman spectra before doing the difference analysis, fluctuations can be compensated, e.g. of alignment, light source intensity fluctuations, etc.

Accordingly in one embodiment, a detection method or detector as described in FIG. 1A or 2A is provided wherein the nitrosamine is N-nitrosodiethanolamine (NDELA), the first wavelength $\lambda1$ is 244 nm, and the calculating the resonance Raman signal (S1) comprises calculating a spectral intensity at a Raman shift of 1410 cm$^{-1}$.

In the present methods, the second pump wavelength $\lambda2$ is shifted off resonance with respect to the first pump wavelength $\lambda1$. The shift is preferably sufficient to provide a substantially lowered resonance Raman signal S2 compared to the resonance Raman signal S1, e.g. wherein the resonance signal S1 is lowered by more than 20%, preferably more than 50%, most preferably more than 80% or even 100%, i.e. completely off-resonance. For example, the off-resonance wavelength $\lambda2$ is shifted at least 10 nm away from the on-resonance wavelength $\lambda1$, preferably more than 15 nm, e.g. 20 nm or more. Typically, it can be desired that the shift is not so large as to substantially affect the non-resonant background. Therefore a wavelength difference between $\lambda1$ and $\lambda2$ is preferably less than 100 nm, more preferably less than 60 nm.

The following table may provide some indication for preferred ranges of the dual pump wavelengths $\lambda1$ and $\lambda2$ for different analytes or chemical groups as well as a suggested location of a strong peak in the Raman spectrum that can be used to probe the analyte.

| Chemical | λ1 (nm) | λ2 (nm) | Raman shift (cm−1) of strong peak |
|---|---|---|---|
| Nitrosamine | 240-250 | 260-300 | 1410 |
| Nitrate | 200-230 | 250-300 | 1044 |
| Nitrite | 210-240 | 250-300 | 1325 |
| RDX | 250-260 | 270-300 | 924 |
| HMX | 250-260 | 270-300 | 940 |
| PETN | 200-230 | 250-300 | 1292 |
| Anthracene | 240-266 | 270-300 | 1400 |

Of course, also other available peaks or combinations of peaks of the Raman spectrum can be used for probing the analyte. Furthermore, the second pump wavelength $\lambda2$ can be also be further shifted off-resonance, though possibly at the cost of a less suitable reference spectrum I2, e.g. having also a changing background.

In the present example, the non-resonant background Q1 of the first Raman spectrum I1 is similar to the non-resonant background Q2 of the second Raman spectrum I2, except for noise Ns. On the other hand, the resonant signal S1 is more pronounced in the first Raman spectrum I1 than the reference signal in the second Raman spectrum I2. By the difference analysis between the first and second Raman spectra I1,I2, the resonance Raman signal S1 can thus be better isolated from the background Q1.

In one embodiment, the calculating the resonance Raman signal S1 comprises using the second Raman spectrum I2 for reducing the first background Q1 in the first Raman spectrum I1. In one example, the difference analysis comprises subtracting the intensity signal of the second spectrum I2 from that of the first spectrum I1 for all wavelengths resulting in a difference spectrum $\Delta I=I1-I2$. Alternatively or in addition, the difference analysis comprises dividing the intensity signal of the first Raman spectrum I1 by that of the second Raman spectrum I2 for all wavelengths resulting in a quotient spectrum I1/I2 of the first and second 14 amine solvent e.g. as shown in FIG. 3.

Figure 3:
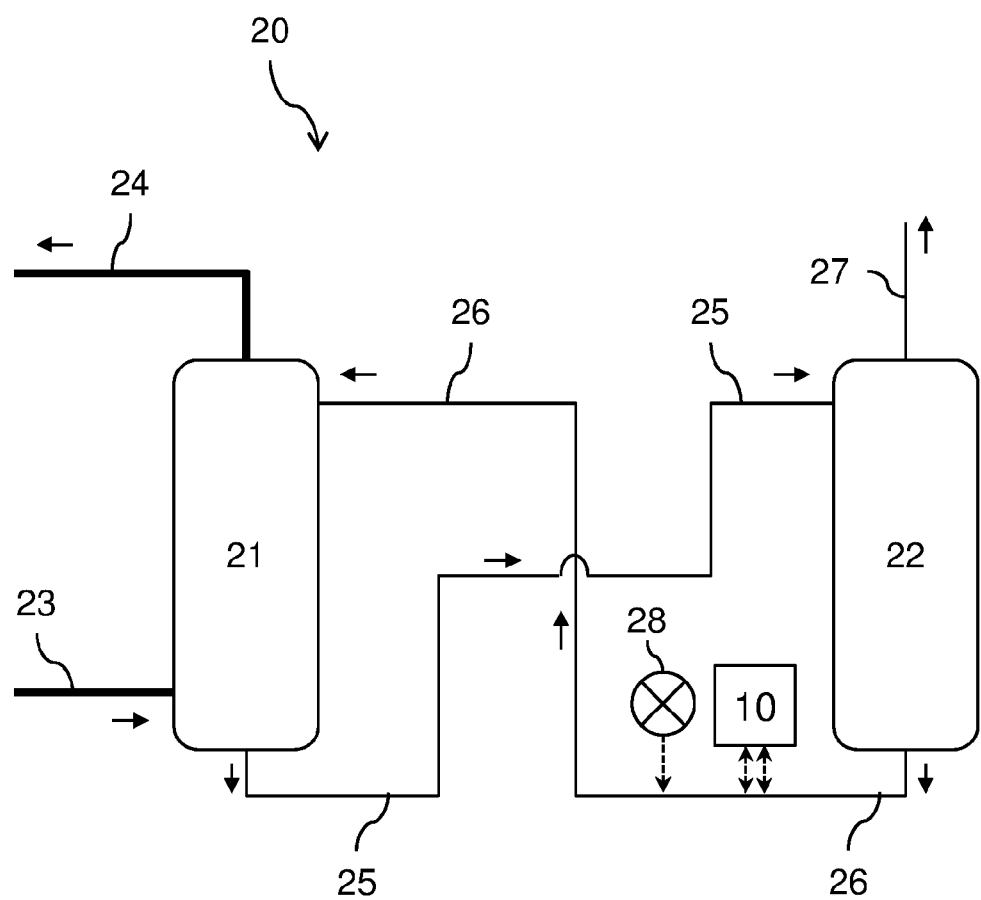
FIG. 3 schematically shows a carbon capture plant.

FIG. 3 schematically shows a carbon capture plant 20 for the separation of carbon dioxide from a flue gas, e.g. produced by combustion of carbohydrates. The carbon capture plant 20 comprises an absorber 21 arranged for containing an amine solvent and flowing the flue gas from a flue gas inlet 23 via the amine solvent to a flue gas outlet 24 for adsorbing the carbon dioxide in the amine solvent. The carbon capture plant 20 further comprises a desorber 22 arranged for regenerating the carbon dioxide loaded amine solvent and separating the carbon dioxide. A first conduit 25 is arranged for transporting the carbon dioxide loaded amine solvent from the absorber 21 to the desorber 22. A second conduit 26 is arranged for transporting the regenerated amine solvent fed back from the desorber 22 to the absorber 21. An outlet 27 of the desorber 22 is arranged for transporting the separated carbon dioxide, e.g. to a storage reservoir.

In one embodiment, the carbon capture plant 20 for the capture of carbon dioxide from a flue gas by means of an amine solvent, comprises a detector 10 arranged for detecting presence of nitrosamine in the amine solvent as described herein, e.g. with reference to FIG. 1A and/or 1B.

In one embodiment a carbon capture process comprises providing a flue gas comprising carbon dioxide, providing an amine solvent, and passing the flue gas via the amine solvent for dissolving carbon dioxide from the flue gas into the amine solvent. Furthermore the process comprises providing the amine solvent in a sample volume 2 and using a method or detector 10 as described herein for detecting presence of nitrosamine as analyte 1 in the sample volume 2.

In a further embodiment, the process comprises adjusting the carbon capture process if the presence of nitrosamine is detected above a threshold level. For example one or more measures can be taken to prevent a further generation of nitrosamine, to prevent escape of the amine solvent, to prevent exposure to the amine solvent, et cetera.

In one embodiment, the carbon capture process comprises switching a UV light source 28 arranged to illuminate the amine solvent when a nitrosamine concentration above a pre-set threshold is detected. For example in one embodiment the carbon capture plant 20 comprises a UV light source 28 arranged for irradiating the amine solvent. A processor is arranged for increasing a UV radiation dose of the UV light source to the amine solvent if the presence of nitrosamine is detected above a threshold level for breaking down the nitrosamine.

In an advantageous embodiment the UV light source 28 comprises the first and/or second light source 11,12 of the detector 10, e.g. as described with reference to FIG. 1. In other words the light source 28 can be integrated in the nitrosamine detector as one or both of the first and/or second light sources for generating the Raman signals. By using the same UV light source for generating a Raman spectrum and neutralizing the nitrosamine concentration, an advantageous combination is obtained. In one embodiment, an intensity of a radiation dose of the UV light source to the amine solvent is varied depending on the detection of nitrosamine.

For example, WO2013023919 describes a method for purification of a nitrosamine-contaminated product from a process plant by using a UV light source and/or changing a pH value which methods can be advantageously used in combination with the presently disclosed detectors and detection methods. For purifying the nitrosamine-contaminated product, preferably, the wavelength of the UV light source 28 is between 180 and 350 nm, more preferably between 220 and 280 nm. It will be appreciated that the same UV light, e.g. at 244 nm, can thus be used for both measuring the presence of nitrosamine and destroying the nitrosamine when found. Preferably a radiation time is set between 2 and 500 minutes. Preferably a pH value is set between 6 and 12, more preferably between 8 and 10.

Without being bound by theory, further elucidation may be obtained from the below description providing a theoretical framework, advantageous examples of analysis methods, practical applications, and measurements performed using the disclosed methods and systems.

Figure 4:
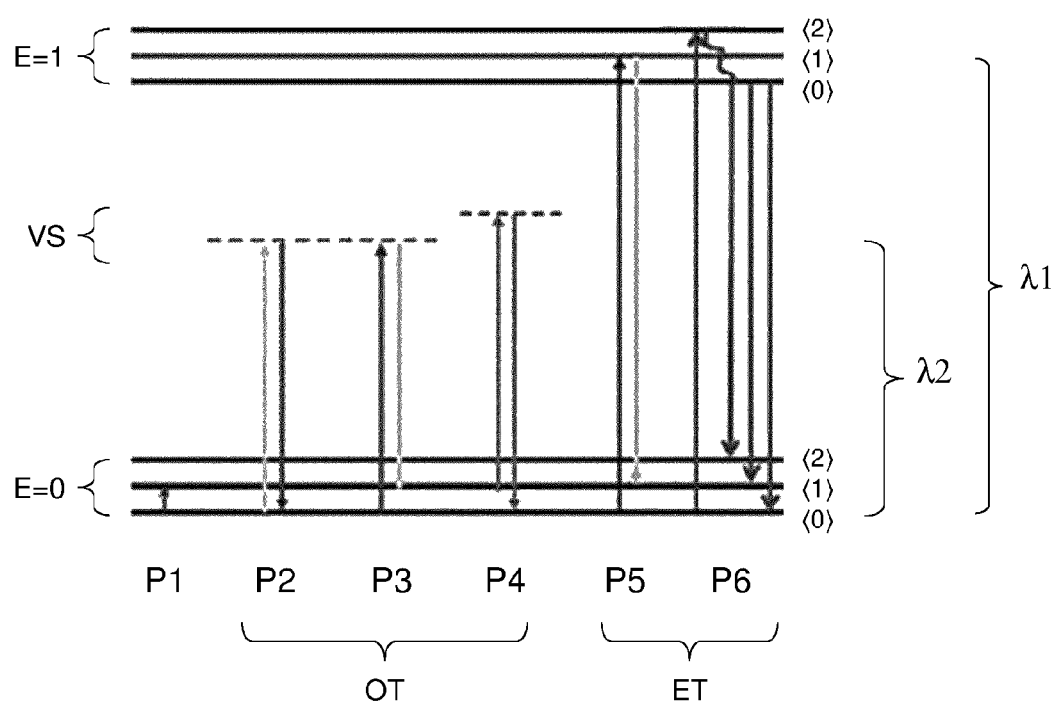
FIG. 4 illustrates an energy level diagram.

FIG. 4 illustrates an energy level diagram. The concept of Raman spectroscopy may be further elucidated with reference to the energy level diagram. The figure shows a number of different processes P1 . . . P6 that can change the energy state of the system by means of a light-matter interaction, e.g. absorption and/or emission of photons. In the diagram, the reference E=0 indicates an electronic ground state and E=1 an electronically excited state of the system. As shown the electronic states can be further divided for example into vibrational states <0>, <1>, <2>. Process P1 indicates a transition from vibrational ground state <0> to a vibrational first excited state <1>. The transition can be spontaneous or stimulated by a photon matching the energy difference between the vibrational states.

Processes P2 . . . P4 illustrate examples of an off-resonance Raman process with off-resonance transitions OT. In such a process, the photon energy or wavelength λ2 does not match a real electronic transition and the system is pumped to a virtual intermediate state VS. It may be considered that a virtual state VS is not an eigenstate of the molecule or system and it can not be occupied but it does allow for transitions between otherwise uncoupled real states. In the process P2, also known as Rayleigh scattering, the system returns to its original state (ground state <0>) and the scattered photon energy is equal to the pump photon energy λ2. In the process P3, also known as Stokes Raman scattering, the system starts in the vibrational ground state <0> and returns in a vibrational excited state <1>. The scattered photon energy is lower than the pump photon energy λ2, wherein the energy difference between the pump photon and scattered photon equals the energy difference between the vibrational states <0> and <1>. It will be appreciated that the scattered photon energy or wavelength can be measured to determine the energy difference and provide information on the vibrational states of the system. In the process P4, known as Anti-stokes Raman scattering the system starts in a vibrational excited state <1> and returns in a vibrational ground state <0>. The scattered photon energy is higher than the pump photon energy λ2, wherein the energy difference between the pump photon and scattered photon equals the energy difference between the vibrational states <0> and <1>.

Processes P5 and P6 illustrate examples of resonance Raman processes with electronic transitions ET. In such a process, the photon energy or wavelength λ2 matches a real electronic transition and the system is pumped to an electronically excited state (E=0→1). The process P5 illustrates a resonance Stokes Raman scattering process wherein the system is pumped by a photon of energy λ1 from the electronic ground state E=0 and vibrational ground state <0> to the electronically excited state E=1 in a vibrational excited state <1>. The photon λ1 matches the energy difference between these states. When the system decays back to the electronic ground state a photon is emitted with an energy lower than the pump energy λ1, wherein the energy difference between the pump photon and scattered photon equals the energy difference between the vibrational states <0> and <1>. The process P6 illustrates another resonance Stokes Raman scattering process. In the process P6, the system is pumped from the electronic ground state E=0 and vibrational ground state <0> to the electronically excited state E=1 in a vibrational excited state <2>. The system decays from the vibrational excited state <2> to the vibrational ground state <0> while staying in the electronically excited state E=1. The system then decays to the electronic ground state E=0 into either the vibrational ground state <0>, the first excited vibrational state <1>, or the second excited vibrational state <2>. These three processes may be associated with different photon energies matching the respective energy differences.

The total signal, I, measured in a Raman spectrum can be described as $$I(\bar{v},\lambda,c)=M(\bar{v},\lambda)[S(\bar{v},\lambda,c)+Q(\bar{v},\lambda)]+B(\bar{v},\lambda) \quad (1)$$

where $\bar{v}$ is the Raman shift, $\lambda$ is the incident wavelength, c is the concentration of the analyte, M is the optical response of the system, S is the Raman signal of the analyte and Q is the Raman signal of all other species in the sample, and B is the background.

In resonance Raman spectroscopy, S is enhanced relative to Q when the wavelength of the incident laser source is resonant with an electronic transition of the analyte but not the other species. In some cases, this enhancement alone can be enough to discriminate S from Q by inspection, even without prior knowledge of Q. However, at low concentrations and in samples with complex spectra this approach can be difficult and/or unfeasible. In some situations, Q can be measured independently, but this is not always possible, e.g. with changing concentrations. Chemometric techniques such as principal component analysis can aid in the deconvolution of S from Q but may require multiple samples to be effective.

One concept behind Dual Pump Resonance Raman (DP-RR) as described herein is that S and Q exhibit different functional dependences on the incident wavelength, i.e. $dS/d\lambda > dQ/d\lambda$. I is measured at two wavelengths, $\lambda_1$ and $\lambda_2$, and the two responses, $I_1$ and $I_2$ are given by $$I_1(\bar{v},c)=M_1(\bar{v})[S_1(\bar{v},c)+Q_1(\bar{v})]+B_1(\bar{v})$$

$$I_2(\bar{v},c)=M_2(\bar{v})[S_2(\bar{v},c)+Q_2(\bar{v})]+B_2(\bar{v}) \quad (2)$$

where

The background and optical response terms are measurable constants. We define the normalized intensity, $I_{norm}=(I-B)/M$. The difference in the two signals, $\Delta I_{norm}$, is given by $$\Delta I_{norm}(\bar{v},c) = I_{norm,1}(\bar{v},c) - I_{norm,2}(\bar{v},c) = \Delta S(\bar{v},c) + \Delta Q(\bar{v}) \quad (3)$$

and the quotient, $r_{norm}$, is given by $$r_{norm}(\bar{v},c) = \frac{I_{norm,1}(\bar{v},c)}{I_{norm,2}(\bar{v},c)} = \frac{S_1(\bar{v},c) + Q_1(\bar{v})}{S_2(\bar{v},c) + Q_2(\bar{v})} \quad (4)$$

The decision whether to measure the quotient or ratio of $I_1$ and $I_2$ can depend upon the magnitude of $\Delta Q$; i.e. the variation in the background spectra, as discussed below for simulated spectra.

Figure 5A:
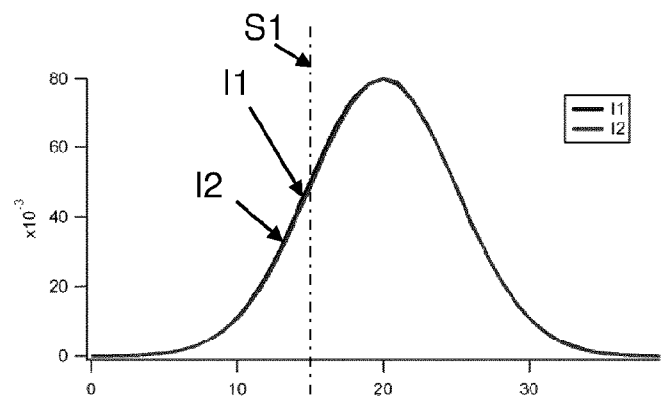
FIG. 5A-5C illustrate a first difference analysis.
Figure 5B:
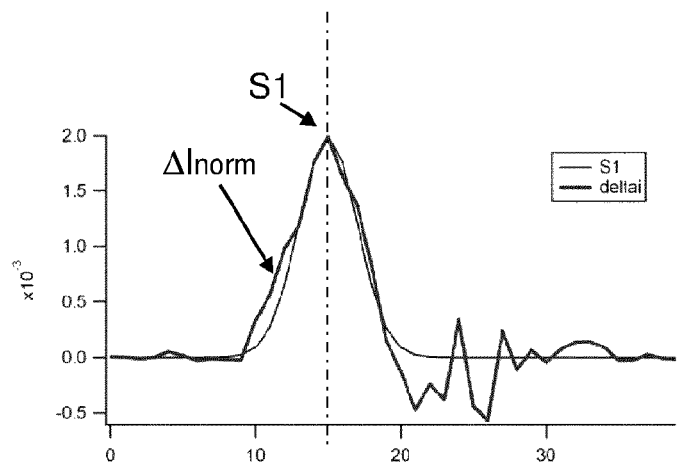
Figure 5C:
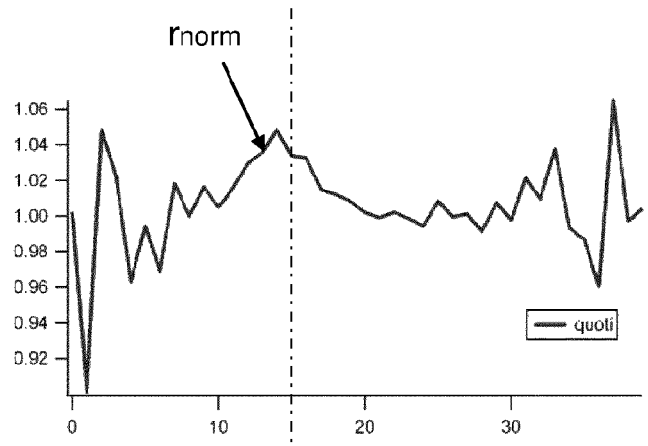

FIG. 5A-5C illustrate a first difference analysis wherein $\Delta Q=0$. FIG. 5A shows the simulated spectra, I1 and I2. The simulated spectra I1, I2 comprise Gaussian background peaks and a small signal S1, with Gaussian noise added that is scaled by $I^{0.5}$ to simulate shot noise. The noise $\sim 0.1 S1$ and the signal $S1 \sim 0.01\ Q1$. S1 and Q1 are offset by the width of Q1. FIG. 5B shows the simulated signal, S1 and a difference spectrum $\Delta I_{norm}=I1-I2$. FIG. 5C shows a quotient spectrum $r_{norm}=I1/I2$. For simplicity we assume here that $S_2=0$. This assumption will hold if $\lambda_2$ is sufficiently far from the resonance wavelength of the analyte, and if the analyte concentration is low. This situation is most relevant for DP-RR in any case, as at high c the signal can be determined by inspection. If $\Delta Q=0$, then $$\Delta I_{norm}(\bar{v},c) = S_1(\bar{v},c)$$

whereas $$r_{norm}(\bar{v},c) = 1 + \frac{S_1(\bar{v},c)}{Q(\bar{v})}$$

$\Delta I_{norm}$ and $r_{norm}$ are shown for simulated spectra in the figures. The signal is barely visible as a small shoulder on the main peak in I1 of FIG. 4B. This response can be representative of a weak signal peak in a real sample. However, the determination of the reference spectrum I2 readily allows the extraction of a readily-quantifiable signal in $\Delta I_{norm}$. In this case, the signal to noise ratio (SNR) is greater for $\Delta I_{norm}$ than $r_{norm}$.

Figure 6A:
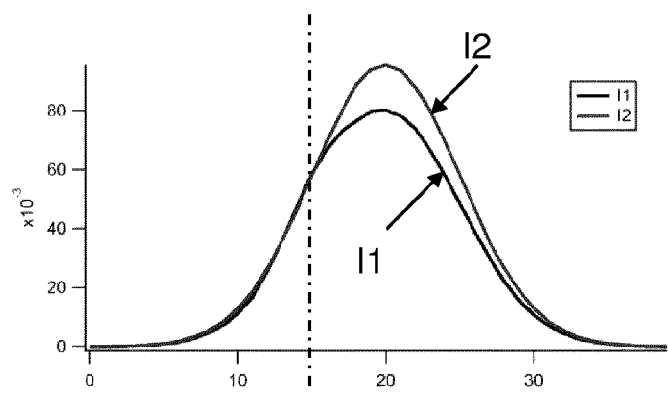
FIG. 6A-6C illustrate a second difference analysis.
Figure 6B:
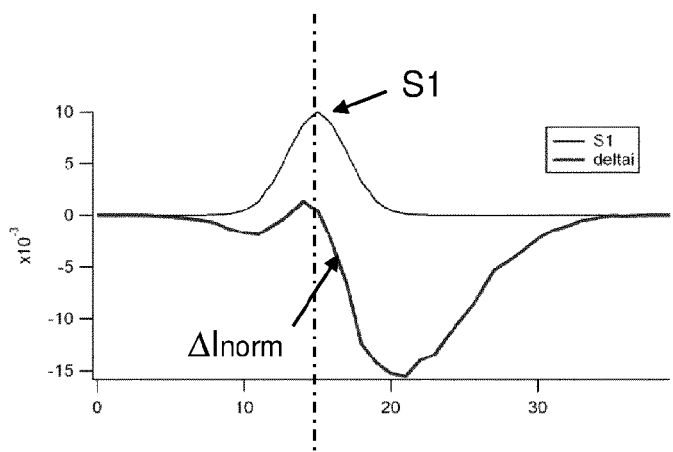
Figure 6C:
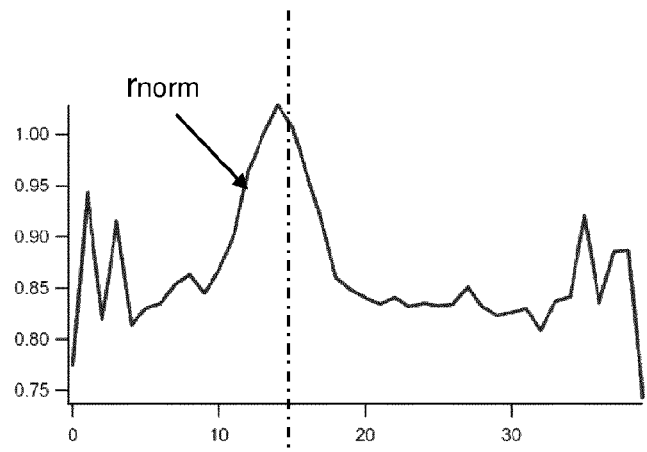

FIG. 6A-6C illustrate a second difference analysis wherein $\Delta Q \neq 0$. The spectra I1 and I2 comprise Gaussian peaks, with Gaussian noise added that is scaled by $I^{0.5}$ to simulate shot noise. Noise$\sim 0.05 I1$. $I1 \sim 0.05\ Q_1$. $Q_2=1.2\ Q_1$. I1 and $Q_1$ offset by width of $Q_1$. FIG. 6A shows the simulated spectra, $I_1$ and $I_2$. FIG. 6B shows the simulated signal, $S_1$ and the difference spectrum $\Delta I$, FIG. 6C shows the quotient spectrum $r_{norm}$.

If the two signals are not well-matched in amplitude, but the backgrounds exhibit the same shape, then $$\Delta I_{norm}(\bar{v},c) = S_1(\bar{v},c) + \Delta Q(\bar{v})$$

whereas $$r_{norm}(\bar{v},c) = \frac{S_1(\bar{v},c) + Q_1(\bar{v})}{Q_2(\bar{v})}$$

As illustrated by these figures, the larger the difference in $\Delta Q$, the poorer the signal contrast becomes for $\Delta I_{norm}$. In this case, $r_{norm}$ is a better measurement for determining the signal S1. In practice, both $\Delta I_{norm}$ and $r_{norm}$ can be calculated.

In one embodiment, with reference to FIG. 2A, the method or detector can be realized in the following way:

1. The spectrograph 15 is frequency-calibrated to determine the correct Raman shift at each incident laser wavelength.
2. The spectrograph 15 is intensity-calibrated to determine B and M at each incident laser wavelength.
3. Two laser sources 11 and 12 (e.g. 244 and 266 nm) are focused onto the sample such that the foci f1 and f2 are offset by e.g. 300 μm (less than the field of view of the focussing lens 6, but greater than the resolution of a detecting element 4).
4. The foci are imaged onto the spectrograph slit 14 and ultimately the CCD 4 such that the spectra are offset along 4y perpendicular to the dispersion axis 4x.
5. The magnification of the imaging system (e.g. 4×) will offset the spectra, in this case by 1200 μm (~60 pixels in a typical CCD array).
6. The software controlling the CCD array reads out each spectrum independently and calculates $\Delta I_{norm}$ and $r_{norm}$.
7. $\Delta I_{norm}$ and $r_{norm}$ are proportional to c, giving the relative concentration of the analyte.

Figure 7A:
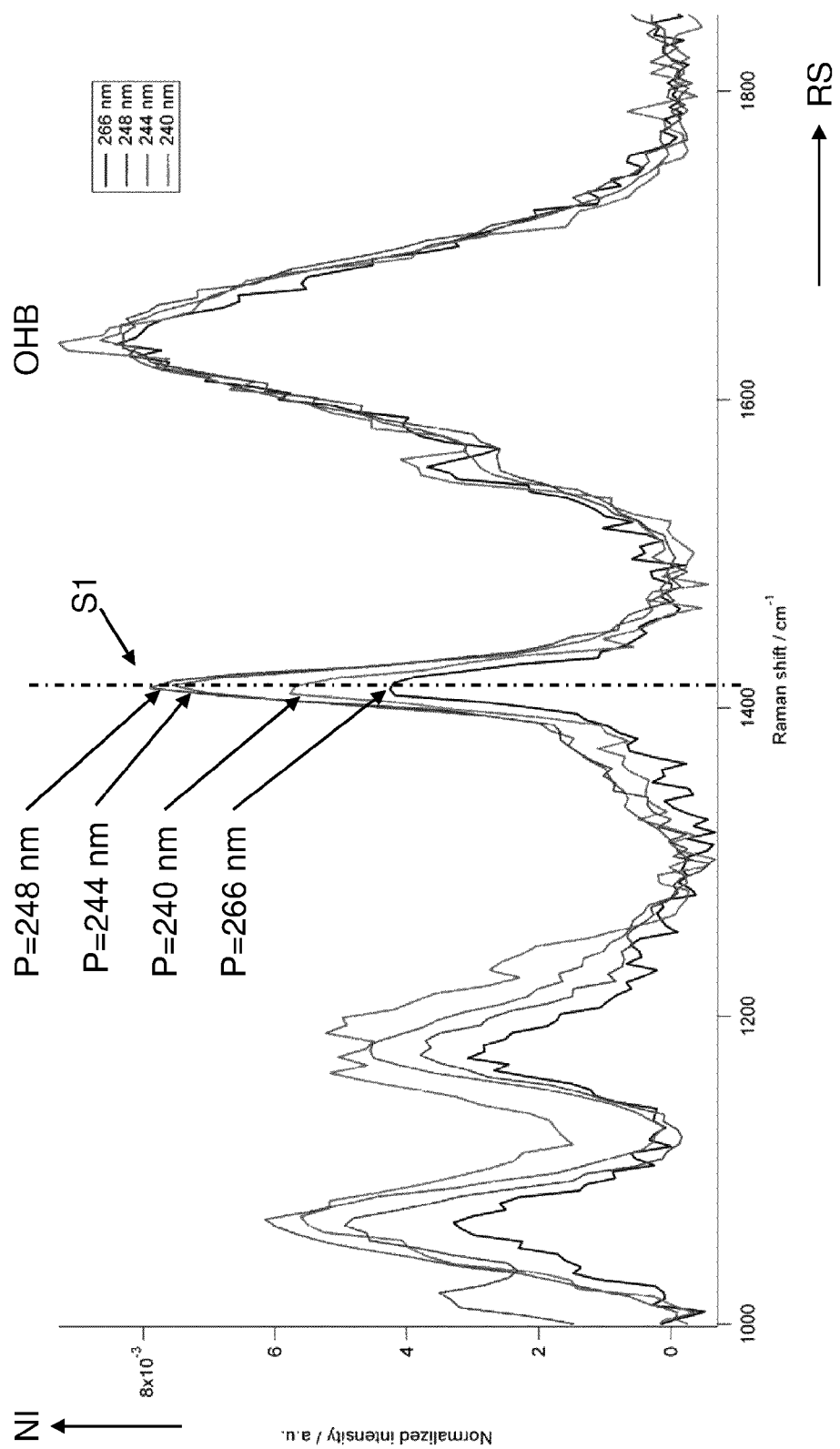
FIG. 7A shows Resonance Raman spectra at different pump wavelengths.

FIG. 7A shows deep UV Resonance Raman (RR) spectra of solutions of NDELA in water at 100 ppm taken with incident laser wavelengths of 240, 244, 248 and 266 nm. At 266 nm, the water bend at $\sim 1630\ cm^{-1}$, the nitroso peak at $1410\ cm^{-1}$ and the Si—O stretches at 1070 and $1170\ cm^{-1}$ from the fused silica cuvette that contains the solution are clearly visible. The nitroso peak is approximately twice as intense at 244 and 248 nm as at 266 nm. However, the signal level actually decreases at 240 nm. This result can be due to greater reabsorption of the Raman scattered light at 240 nm by the solution, and/or due to greater photochemical reactions reducing the actual NDELA concentration. The optimum wavelength for RR spectroscopy of NDELA solutions is thus found to be around 244-248 nm.

Figure 7B:
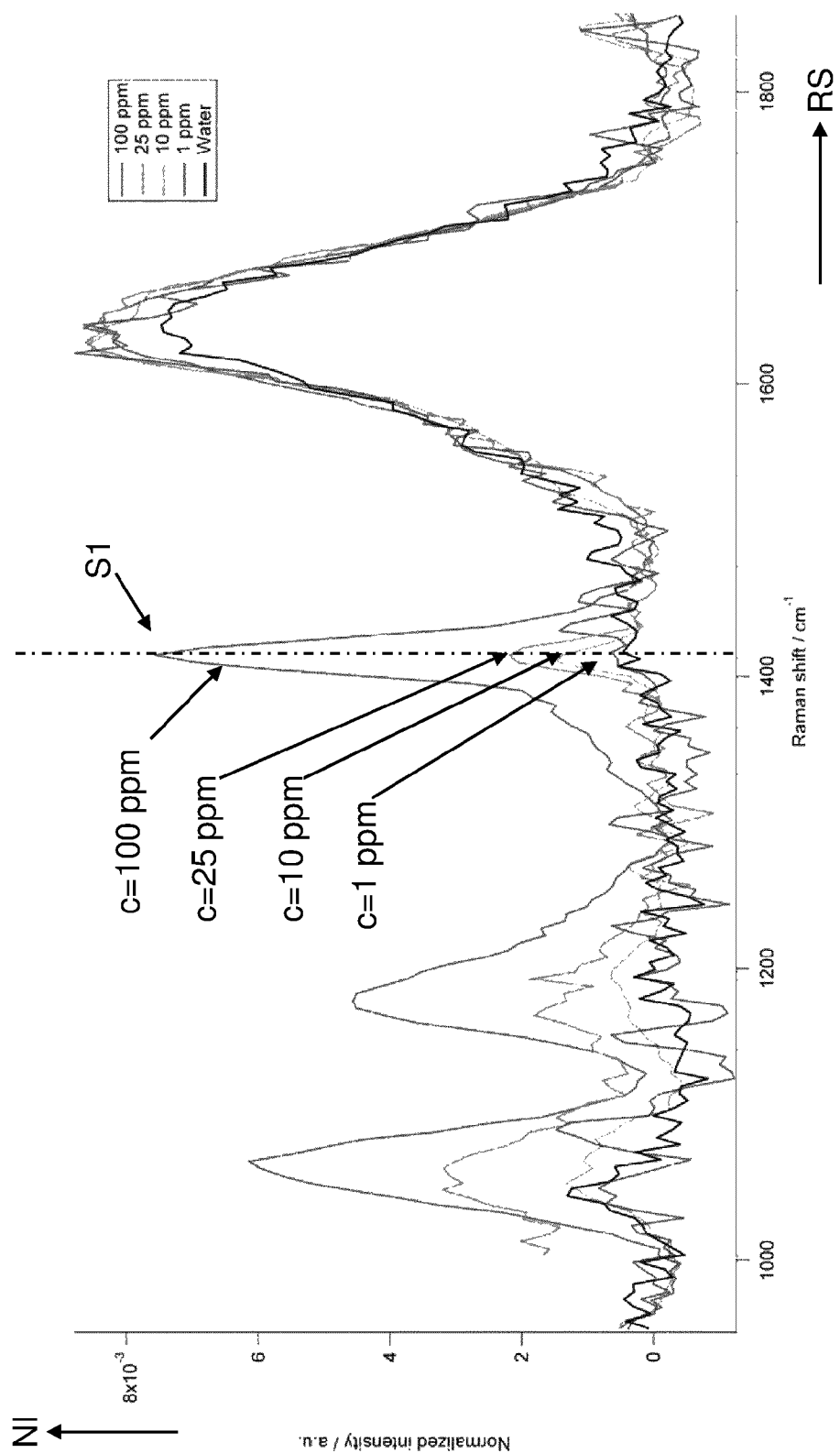
FIG. 7B shows Resonance Raman spectra at different analyte concentrations.

FIG. 7B shows RR spectra of NDELA solutions in water at concentrations between 1 and 100 ppm taken with an incident laser wavelength of 244 nm. The nitroso signal is clearly visible above the noise level at 10 ppm and can be further improved e.g. by the dual pump technique as described herein.

Figure 8A:
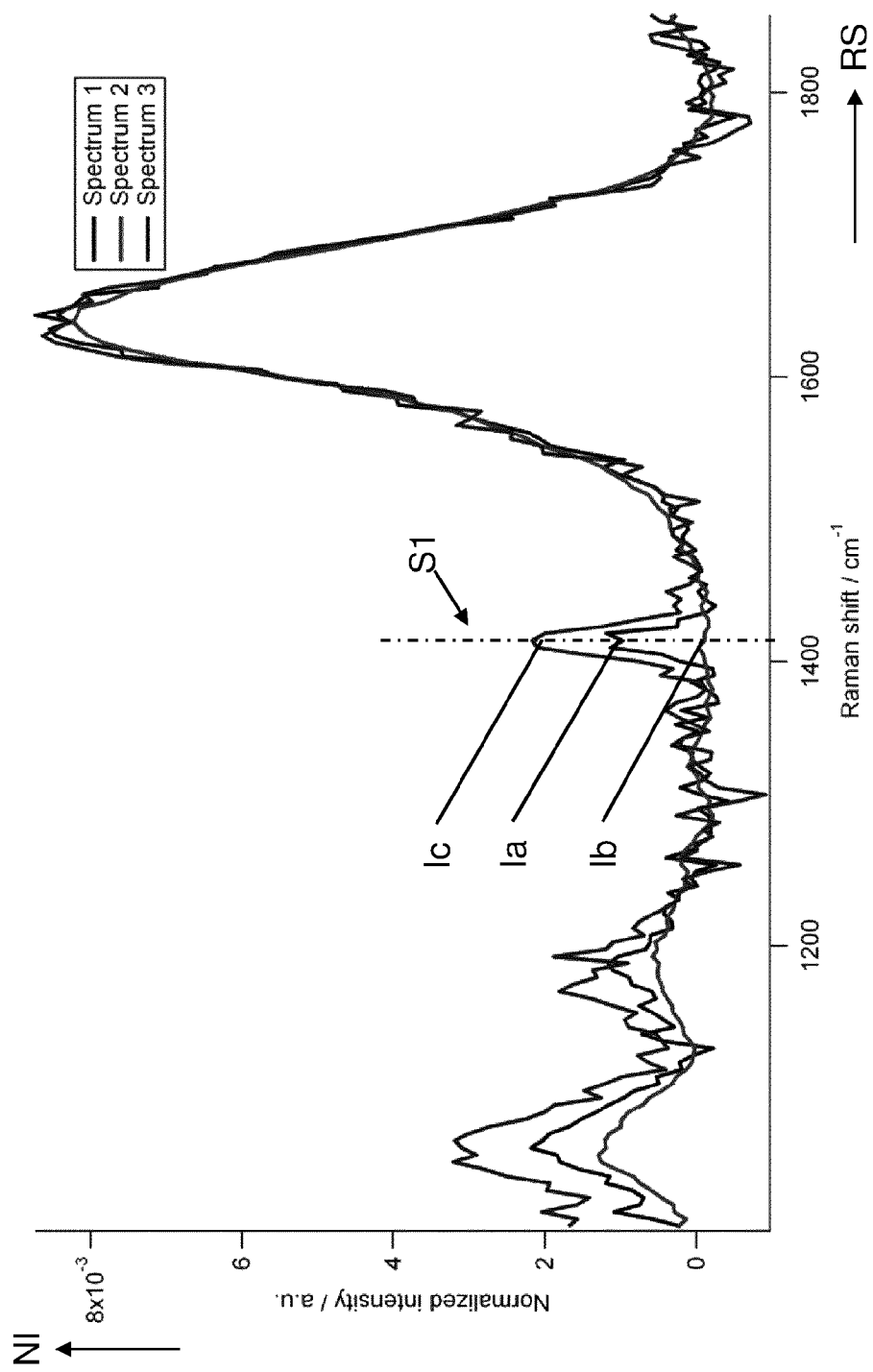
FIG. 8A shows Resonance Raman spectra at different laser powers.

FIG. 8A shows RR spectra of a 25-ppm NDELA solution in water at different laser powers at 244 nm pump wavelength. The laser power was increased by a factor of four between spectrum Ia and spectrum Ib. The laser power was reduced to the original level for spectrum Ic. All other acquisition conditions were the same for all spectra.

As shown, the increase in laser power for spectrum Ib has actually caused a decrease in the nitroso peak intensity. Although the UV light gives a boost in Raman signal through resonant enhancement, it can also initiate photochemical degradation. In this case, the 244-nm photons have reduced the local concentration of nitroso groups in the laser focus to below the detection limit. Reducing the laser power again enables the signal to recover as unreacted NDELA diffuses back into the laser focus. Accordingly it is shown that the 244-nm laser light may be used to destroy NDELA, e.g. in an embodiment as was described with reference to FIG. 2. Furthermore, the laser may already be limiting the nitroso peak intensity, even at the reduced powers employed in spectra Ia and Ic. However, the incorporation of a flow system can allow the maximum signal level to be determined, as the solution will then be continually refreshed.

Figure 8B:
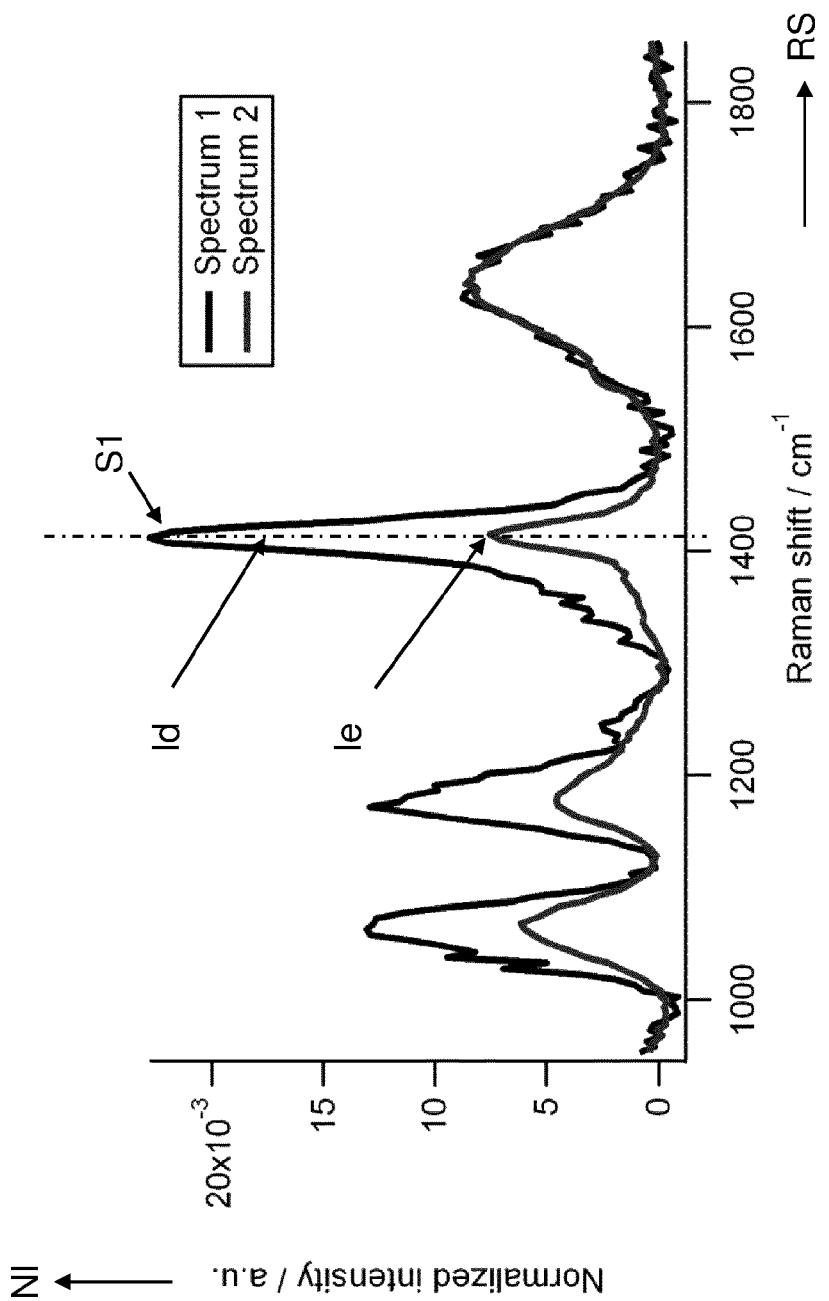
FIG. 8B shows Resonance Raman spectra measure with a time interval.

FIG. 8B shows RR spectra of 100 ppm NDELA in water (aq.) solutions with a 24 hour interval between the measurements at ambient conditions. This illustrates that NDELA can degrade at ambient conditions over time. Spectrum Id was taken on the first day of measurements, whereas spectrum Ie was taken approximately 24 hours later. It is shown that the nitroso peak has decreased appreciably during this time. Accordingly, in one embodiment, to reduce a concentration of nitrosamine after detection, the amine solution is stored for a period of time to let the nitrosamine concentration degrade until the said concentration is determined to be below a preset limit.

Figure 9:
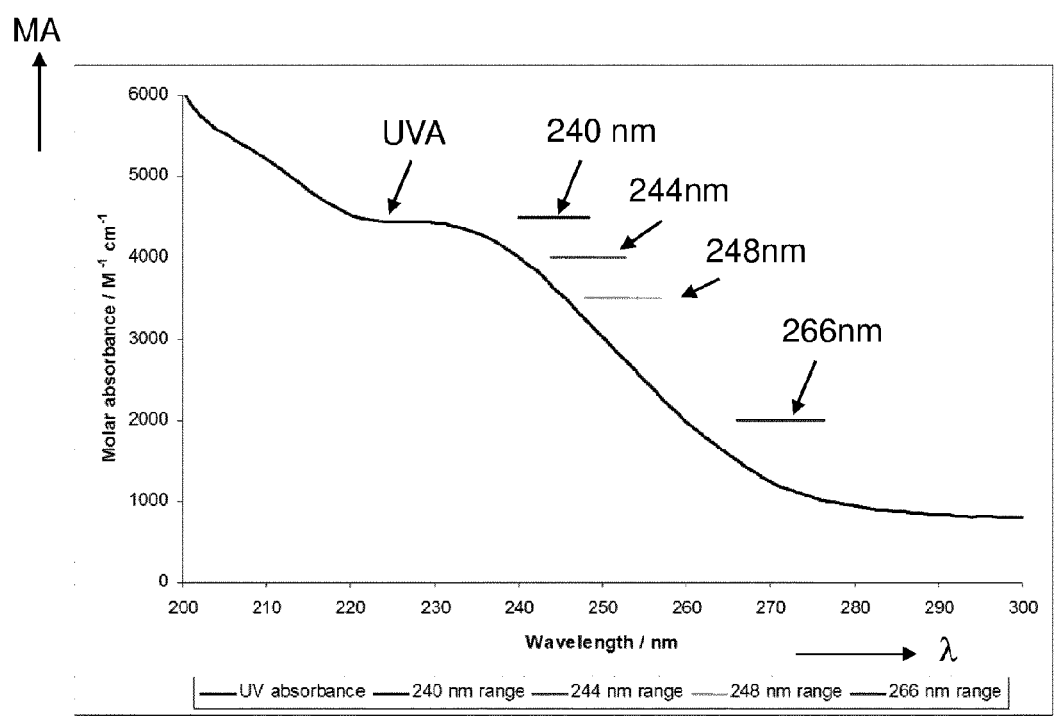
FIG. 9 shows a UV absorbance spectrum.

FIG. 9 shows a UV absorbance spectrum of 10 ppm NDELA (aq.). The incident UV wavelengths as discussed herein and the extent of the Raman scattered light at these wavelengths are also shown in the figure for reference. NDELA has a reasonably strong molar absorbance (MA) of ~4000 $M^{-1}$ $cm^{-1}$ at a wavelength ($\lambda$) of 235 nm. It will be understood that the strength of the resonance enhancement effect in the RR spectrum can be dependent upon the magnitude of this molar absorbance. On the other hand, a strong absorption of the scattered UV light may impede measurement of the Raman spectrum.

While example embodiments were shown for a method and detector, also alternative ways may be envisaged by those skilled in the art having the benefit of the present disclosure for achieving a similar function and result. E.g. electronic and/or optical components may be combined or split up into one or more alternative components. The various elements of the embodiments as discussed and shown offer certain advantages, such as providing an enhanced detection method. Of course, it is to be appreciated that any one of the above embodiments or processes may be combined with one or more other embodiments or processes to provide even further improvements in finding and matching designs and advantages. It is appreciated that this disclosure offers particular advantages to detection of nitrosamine in an amine solvent, and in general can be applied for any application wherein a background can be subtracted for improving a signal.

The inventors have found a specific optical wavelength (244 nm) that is suitable to obtain a Resonance Raman peak for NDELA (at 1410 $cm^{-1}$). From the Raman spectrum that is obtained with this wavelength the inventor can deduce the concentration of NDELA from the peak at 1410 $cm^{-1}$, MEA from the peak at 1460 $cm^{-1}$ and $CO_2$ from the peak at 1015 $cm^{-1}$.

Besides advantageous application in a carbon capture process, also other processes may benefit from the detection of nitrosamine as a carcinogenic compound. For example, a food inspection method comprising providing a food product in a sample volume; using a detection method or detector as described herein for detecting presence of nitrosamine as analyte in the sample volume; and treating and/or discarding the food product if the presence of nitrosamine is detected above a threshold level.

Furthermore, it will be appreciated that the dual-pump approach discussed herein could also be applied in other spectroscopies in which it is difficult to isolate the signal of a low-concentration species. Alternative to using a spectrograph and CCD detector, the costs of the detector can be reduced through the incorporation of band-pass filters in place of spectrograph and/or photodiodes in place of CCD detector. This approach may limit the bandwidth to one peak though if the vibrational frequency of the analyte is known in advance, the choice of band-pass filter is straightforward. Usually this single-frequency approach is limited in Raman by lack of knowledge of the baseline under the peak of interest. This problem can be circumvented using the DP-RR approach. Furthermore it may be advantageous to replace the laser source(s) with (UV-) LED(s).

Alternatively or in addition, the concept of DP-RR can be extended to analytes that can be resonantly enhanced in the near-UV and visible regions of the electromagnetic spectrum. Performing resonant Raman spectroscopy with these longer wavelengths is usually complicated by the presence of fluorescence. Fluorescence creates a large, sloping background beneath the Raman peaks, as well as introducing shot-noise that degrades the quality of the Raman spectrum. One approach to remove the fluorescence is based on time-gating, in which the differing time responses of the Raman and fluorescence processes are used to separate these signals in the time domain. This approach can be combined with the single-frequency DP-RR concept to extend DP-RR into the near-UV-visible region.

Alternatively or in addition to using the dual-pump approach as described herein, surface-enhanced resonance Raman spectroscopy (SERRS) is the resonantly-enhanced version of surface-enhanced Raman spectroscopy (SERS). In SERRS, as well as the surface-enhancement from the roughened metal substrate, further enhancement arises from electronic resonance between the adsorbed chromophore and the pump laser. SERRS is exquisitely sensitive, with single-molecule detection being reported, but nevertheless, it is still important to distinguish the SERRS photons from the normal Raman scattering of the solvent or surrounding matrix. The dual-pump approach could also play a significant role here to help distinguish these signal and background responses.

While the present systems and methods have thus been described in particular detail with reference to specific exemplary embodiments thereof, it should also be appreciated that numerous modifications and alternative embodiments may be devised by those having ordinary skill in the art without departing from the scope of the present disclosure. For example, embodiments wherein devices or systems are disclosed to be arranged and/or constructed for performing a specified method or function inherently disclose the method or function as such and/or in combination with other disclosed embodiments of methods or systems. Furthermore, embodiments of methods are considered to inherently disclose their implementation in respective hardware, where possible, in combination with other disclosed embodiments of methods or systems. Furthermore, methods that can be embodied as program instructions, e.g. on a non-transient computer-readable storage medium, are considered inherently disclosed as such embodiment.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. Method for detecting an analyte in a sample volume, the analyte having an electronic transition (ET), the method comprising
    directing a first light beam (P1) having a first wavelength ($\lambda 1$) into the sample volume, wherein the first wavelength ($\lambda 1$) matches the electronic transition (ET) of the analyte for generating a resonance Raman signal (S1) of the analyte;
    measuring a first Raman spectrum (I1) from the sample volume, the first Raman spectrum (I1) comprising the resonance Raman signal (S1) of the analyte and a first background (Q1) generated by the first light beam (P1) interacting in the sample volume;
    directing a second light beam (P2) having a second wavelength ($\lambda 2$) into the sample volume, wherein the second wavelength ($\lambda 2$) is shifted at least 10 nm with respect to the first wavelength ($\lambda 1$) away from the electronic transition (ET) for generating an off-resonance Raman signal (S2) of the analyte, wherein the off-resonance Raman signal (S2) is lower than the resonance Raman signal (S1);
    measuring a second Raman spectrum (I2) from the sample volume, the second Raman spectrum comprising the off-resonance Raman signal (S2) and a second background (Q2) generated by the second light beam (P2) interacting in the sample volume; and
    calculating the resonance Raman signal (S1) of the analyte from a difference analysis between the first and second Raman spectra (I1, I2).

2. Method according to claim 1 wherein the first and second light beams (P1,P2) generate the resonance Raman signal (S1) and the off-resonance Raman signal (S2) at different locations (f1 ,f2) in the sample volume; wherein the said different locations (f1,f2) are imaged separately.

3. Method according to claim 1, wherein the first and second light beams (P1,P2) are directed simultaneously into the sample volume and the first and second Raman spectra (I1,I2) are measured simultaneously.

4. Method according to claim 1 comprising passing a sample flow through the sample volume while repeatedly calculating the resonance Raman signal (S1) of the analyte.

5. Method according to claim 1, wherein the calculating the resonance Raman signal (S1) comprises using the second Raman spectrum (I2) for reducing the first background (Q1) in the first Raman spectrum (I1).

6. Method according to claim 1, wherein the calculating the resonance Raman signal (S1) comprises one or more of
    calculating a difference spectrum (I1-I2) of the first and second Raman spectra (I1,I2);
    calculating a quotient spectrum (I1-I2) of the first and second Raman spectra (I1,I2);
    performing a principle component analysis (PCA) of the first and second Raman spectra (I1,I2).

7. Carbon capture process comprising
    providing a flue gas comprising carbon dioxide;
    providing an amine solvent;
    passing the flue gas via the amine solvent for dissolving carbon dioxide from the flue gas into the amine solvent;
    providing the amine solvent in a sample volume; and
    using a method according to claim 1 for detecting presence of nitrosamine as analyte in the sample volume.

8. Method according to claim 7, further comprising adjusting the carbon capture process if the presence of nitrosamine is detected above a threshold level.

9. Method according to claim 1, further comprising using off-resonant Raman signals in the first and/or second Raman spectra (I1,I2) for calculating a concentration of amines and/or dissolved carbon dioxide in the sample volume.

10. Nitrosamine detector for detecting presence of a nitrosamine analyte in an amine solvent, the detector comprising
    a sample chamber, arranged for providing the amine solvent in a sample volume;
    a first light source, arranged for directing a first light beam (P1) having a first wavelength ($\lambda 1$) between 240-250 nm into the sample volume, wherein the first wavelength ($\lambda 1$) matches an electronic transition (ET) of the analyte for generating a resonance Raman signal (S1) of the analyte;
    a second light source, arranged for directing a second light beam (P2) having a second wavelength ($\lambda 2$) into the sample volume, wherein the second wavelength ($\lambda 2$) is shifted with respect to the first wavelength ($\lambda 1$) away from the electronic transition (ET) for generating an off-resonance Raman signal (S2) of the analyte, wherein the off-resonance Raman signal (S2) is lower than the resonance Raman signal (S1);
    a first photo detector, arranged for measuring a first Raman spectrum (I1) from the sample volume, the first Raman spectrum (I1) comprising the resonance Raman signal (S1) of the analyte and a first background (Q1) generated by the first light beam (P1) interacting in the sample volume;
    a second photo detector, arranged for measuring a second Raman spectrum (I2) from the sample volume, the second Raman spectrum comprising the off-resonance Raman signal (S2) and a second background (Q2) generated by the second light beam (P2) interacting in the sample volume;
    a processor, arranged for receiving the first and second Raman spectra (I1,I2) from the first and second photo detectors and calculating the resonance Raman signal (S1) of the analyte from a difference analysis between the first and second Raman spectra (I1,I2), and determining a presence and/or concentration of the analyte from the calculated Raman signal (S1).

11. Nitrosamine detector according to claim 10, wherein the calculating the resonance Raman signal (S1) comprises calculating a spectral intensity at a Raman shift of 1410 $cm^{-1}$.

12. Carbon capture plant for the capture of carbon dioxide from a flue gas by means of an amine solvent, the plant comprising a nitrosamine detector according to claim 10 arranged for detecting presence of nitrosamine in the amine solvent.

13. Carbon capture plant according to claim 12, comprising a UV light source arranged for irradiating the amine solvent wherein the processor is arranged for increasing a UV radiation dose of the UV light source to the amine solvent if the presence of nitrosamine is detected above a threshold level for breaking down the nitrosamine.

14. Carbon capture plant according to claim 13, wherein the UV light source comprises the first and/or second light source.

* * * * *